(12) United States Patent
Kaneto et al.

(10) Patent No.: US 7,632,236 B2
(45) Date of Patent: Dec. 15, 2009

(54) CATHETER AND PRODUCTION METHOD THEREOF

(75) Inventors: Masayuki Kaneto, Ibaraki (JP); Yasuhito Ohwaki, Ibaraki (JP); Tetsuya Ohsawa, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 326 days.

(21) Appl. No.: 11/300,517

(22) Filed: Dec. 15, 2005

(65) Prior Publication Data

US 2006/0129061 A1 Jun. 15, 2006

(30) Foreign Application Priority Data

Dec. 15, 2004 (JP) ............... 2004/363322

(51) Int. Cl.
*A61B 5/00* (2006.01)
*A61B 5/02* (2006.01)

(52) U.S. Cl. ............ 600/561; 600/485
(58) Field of Classification Search ........... 600/561; 606/41, 27; 607/116; 257/684
See application file for complete search history.

(56) References Cited

U.S. PATENT DOCUMENTS

| 6,263,229 | B1 | 7/2001 | Atalar et al. | |
| 7,229,437 | B2 * | 6/2007 | Johnson et al. | 606/41 |
| 2003/0020152 | A1 * | 1/2003 | Inoue et al. | 257/684 |
| 2004/0015084 | A1 | 1/2004 | Flesch et al. | |
| 2004/0230114 | A1 | 11/2004 | Clatterbaugh et al. | |

FOREIGN PATENT DOCUMENTS

| EP | 0 377 943 | 7/1990 |
| JP | 9-276236 | 10/1997 |
| JP | 2000-193546 | 7/2000 |
| JP | 2000287944 A * | 10/2000 |
| JP | 2006-167119 | 6/2006 |

OTHER PUBLICATIONS

Patent Abstracts of Japan, vol. 2000, No. 13, Feb. 5, 2001 & JP 2000 287944A, Oct. 17, 2000.
Japanese Office Action dated Sep. 29, 2009 issued in corresponding JP application with English translation.

\* cited by examiner

*Primary Examiner*—Max Hindenburg
*Assistant Examiner*—Brian Szmal
(74) *Attorney, Agent, or Firm*—Wenderoth, Lind & Ponack, L.L.P.

(57) ABSTRACT

The present invention provides a catheter 100 having a structure wherein an electronic component 2 is mounted on the anterior end or an intermediate part of a tube 1, a signal line electrically connecting to the electronic component 2 extends from the vicinity of the electronic component 2 through the aforementioned tube 1 to the posterior end of the aforementioned tube 1, which is characterized in that the signal line consists of a wiring pattern 4 of the flexible printed circuit board 10 inserted in the tube 1. Consequently, an electronic component-loaded catheter can control increase in the size of the tube caused by multiple signal lines to be connected to the electronic component.

9 Claims, 8 Drawing Sheets

CATHETER AND PRODUCTION METHOD THEREOF

FIELD OF THE INVENTION

The present invention relates to a catheter comprising an electronic component in a tube, and a production method thereof.

BACKGROUND OF THE INVENTION

Conventionally, various tests and treatments are performed based on the electrical signals transmitted by electronic components, such as a heat element, a pressure sensor, a temperature measurement thermistor and the like, set in the anterior end or an intermediate part of a tube of a catheter inserted into the body of patients. Such an electronic component-loaded catheter is described, for example, in JP-A-11-56794 and JP-A-2001-170013.

The aforementioned "anterior end of a tube" means an end of the head of a catheter (tube) in the length direction, which is to be inserted into the body of patients, and the "anterior end of a tube" in the following description in the present specification means an end of the head of a catheter (tube) in the length direction when inserted into the body of patients, and the "posterior end of a tube" means the other end of the tube, which is the opposite side from the head, in the length direction.

In the above-mentioned catheter comprising an electronic component in a tube, an electrical signal sent by an electronic component in the anterior end or an intermediate part of a tube inserted in the body of patients is processed by a measuring apparatus etc. connected to the posterior end of the tube outside the body of patients. When the operation of the aforementioned electronic component is to be controlled, it is remotely controlled by a control device connected to the posterior end of a tube outside the body of patients. Therefore, a signal line to transmit an electrical signal between the electronic component and a measuring apparatus, a control device and the like needs to be installed in the tube of an electronic component-loaded catheter. As such signal line, signal cables such as flat cable etc. have been conventionally used, as in the catheters described in the aforementioned JP-A-11-56794 and JP-A-2001-170013. Recently, however, for higher functions of electronic components to be set in a tube, this kind of catheter is required to contain an increased number of signal lines. When the number of signal cables is increased to contain many signal lines, the tube containing the signal cables needs to be made thicker. As a result, problems of lower operability of catheter in the body of patients and increased pain felt by patients during operation of catheter occur.

In view of the above-mentioned situation, the problem to be solved by the present invention is provision of an electronic component-loaded catheter capable of reducing increase in the size of tube that contains an increased number of signal lines to be connected to an electronic component, as well as a production method of a catheter, which is capable of efficiently manufacturing such catheter.

SUMMARY OF THE INVENTION

To solve the above-mentioned problem, the present invention employs the following constitution.

(1) A catheter comprising a tube, an electronic component set in the anterior end or an intermediate part of the tube, and a signal line electrically connected to the electronic component, which extends, through the tube, from the vicinity of the electronic component to the posterior end of the tube, wherein the signal line is formed as a wiring pattern of a flexible printed circuit board inserted in the tube.

(2) The catheter of the above-mentioned (1), wherein the flexible printed circuit board comprises a metal support plate.

(3) The catheter of the above-mentioned (2), wherein the size of the metal support plate in the shorter side direction is smaller than that of a base insulating layer in the shorter side direction, and therefore, both ends of the flexible printed circuit board in the shorter side direction are free of the metal support plate.

(4) The catheter of the above-mentioned (3), wherein the size of the metal support plate in the shorter side direction is 50-2950 µm, and the size of the flexible printed circuit board in the shorter side direction is 100-3000 µm.

(5) The catheter of the above-mentioned (3), wherein the flexible printed circuit board is inserted in the tube with the part free of the metal support plate folded inside.

(6) The catheter of the above-mentioned (1), wherein the wiring pattern on a base insulating layer of the flexible printed circuit board has a terminal part, the electronic component is installed in an area near the terminal part, a terminal of the electronic component and the terminal part formed in the wiring pattern are connected by metal welding or with a conductive adhesive, and the connection part is sealed with a resin.

(7) The catheter of the above-mentioned (1), wherein the wiring pattern on a base insulating layer of the flexible printed circuit board has a terminal part, and the terminal part has a pattern formed by a terminal part positioned nearer to the tip of the tube and a terminal part positioned nearer to the posterior end of the tube, which are alternately arranged.

(8) The catheter of the above-mentioned (1), wherein the wiring pattern on a base insulating layer of the flexible printed circuit board has a terminal part, the electronic component is mounted in an area near the terminal part, and a through hole is formed on a side wall of the tube at the position corresponding to the electronic component.

(9) A production method of a catheter, which comprises
 a step of forming a through hole on the anterior end of a tube or a side wall of an intermediate part of the tube, and inserting, in the tube, a flexible printed circuit board whose size in the longitudinal direction is equivalent to or not less than the length from the through hole to the posterior end of the tube,
 a step of mounting, through the through hole formed on the side wall of the tube, an electronic component in an area near the terminal part formed in a wiring pattern on a base insulating layer of the flexible printed circuit board, and
 a step of connecting a terminal of the electronic component and the terminal part formed on the wiring pattern by metal welding or with a conductive adhesive, and sealing the connection part with a resin.

(10) A production method of a catheter, which comprises
 a step of forming a through hole on the anterior end of a tube or a side wall of an intermediate part of the tube, and preparing a flexible printed circuit board whose size in the longitudinal direction is equivalent to or not less than the length from the through hole to the posterior end of the tube, a step of mounting an electronic component in an area near a terminal part formed on a wiring pattern on a base insulating layer of the flexible printed circuit board, then connecting a terminal of the electronic component and the terminal part formed in the wiring pattern by metal welding or with a conductive adhesive, and a step of inserting the flexible printed circuit board in the tube, and sealing the connection part between the terminal of the electronic component and the terminal part of the wiring pattern with a resin through the through hole.

BRIEF DESCRIPTION OF THE DRAWINGS

FIG. 6(a)-FIG. 6(d) are cross-sectional views showing the steps for one embodiment of the production method of the catheter of the present invention.

FIG. 7(a)-FIG. 7(d) are cross-sectional views showing the steps performed after the steps of FIG. 6(a)-FIG. 6(d).

In the Figures, the symbols show the following. 1; a tube, 2; an electronic component, 3; a base insulating layer, 4; a wiring pattern, 5; a cover insulating layer, 10; a flexible printed circuit board, 100; a catheter

DETAILED DESCRIPTION OF THE INVENTION

To afford multiple signal lines, in the catheter of the present invention, it is only necessary to increase the number of wiring patterns of a flexible printed circuit board inserted in a tube. Since a flexible printed circuit board can carry an increased number of wiring patterns without greatly changing its size, the number of signal lines can be increased without greatly changing the size of the tube. Therefore, according to the present invention, when the number of signal lines is the same as that in conventional catheters, the catheter (tube) can be made smaller and the degraded operability of catheter in the body of patients and pain felt by patients during operation of catheter, which are caused by an increased size of a tube due to multiple signal lines, can be eliminated or reduced.

In addition, by the use of a circuit board having a metal support plate as the above-mentioned flexible printed circuit board, the flexible printed circuit board comes to have higher rigidity, and insertion operation of a flexible printed circuit board into a tube is facilitated. Furthermore, unnecessary bending of a catheter and the like do not occur easily, the catheter can easily advance in a desired direction, and the operability of the catheter in the body of patients is improved further.

In addition, by a constitution wherein a metal support plate having a size in the short side direction (width direction) smaller than that of the shorter side direction of the base insulating layer is used as a metal support plate of the above-mentioned flexible printed circuit board, and both ends of the flexible printed circuit board in the shorter side direction are free of a metal support plate, a flexible printed circuit board can be inserted in a tube with both ends (edges on both sides) in the short side direction folded inside. As a result, damage on the tube inner wall during insertion of a flexible printed circuit board in the tube can be prevented and the size of the tube can be further reduced.

Moreover, by a constitution wherein a terminal part is formed in a wiring pattern on a base insulating layer of the above-mentioned flexible printed circuit board, an electronic component is installed in an area near the terminal part, the terminal of the electronic component and the aforementioned terminal part formed in the wiring pattern are connected by metal welding or with a conductive adhesive, and the connection part is sealed with a resin, a highly reliable catheter can be realized, wherein an electric connection between the electronic component and the wiring pattern (signal line) can be stably maintained even when the catheter is deformed or received an impact during operation of the catheter.

According to the production method of the catheter of the present invention, the catheter of the present invention having a smaller size of the catheter (tube) as compared to conventional catheters can be efficiently produced with a smaller number of steps. In addition, since an electronic component can be mounted on a flexible printed circuit board, the electronic component can be precisely positioned in a tube.

The present invention is explained in more detail in the following by referring to Figures.

Figure 1:
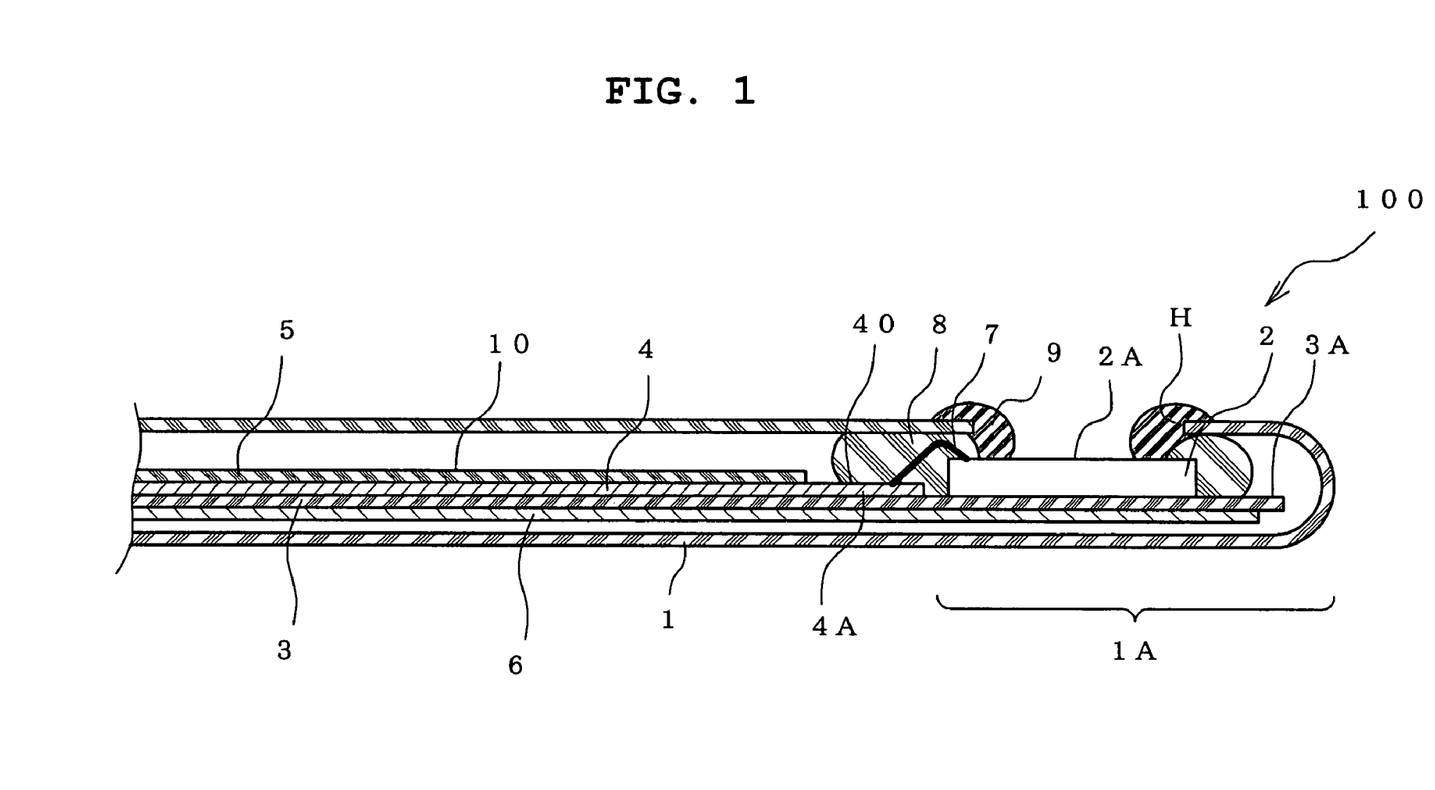
FIG. 1 is a cross-sectional view (longitudinal cross-sectional view) of one embodiment of the catheter of the present invention, along the plane including the axis of the catheter.
Figure 2:
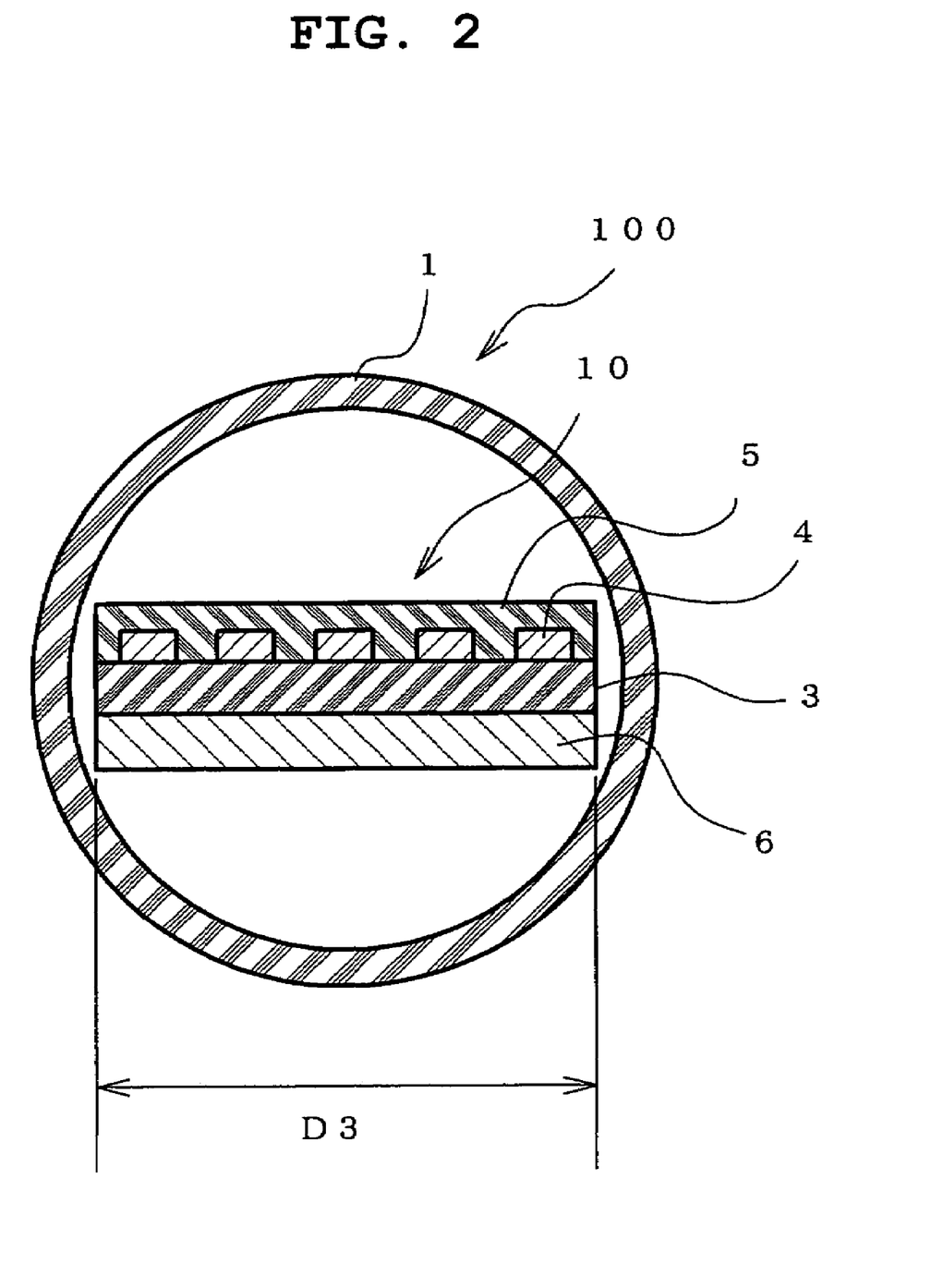
FIG. 2 is a cross-sectional view (transverse cross-sectional view) of one embodiment of the catheter of the present invention, along the plane perpendicular to the axis of the catheter.
Figure 3:
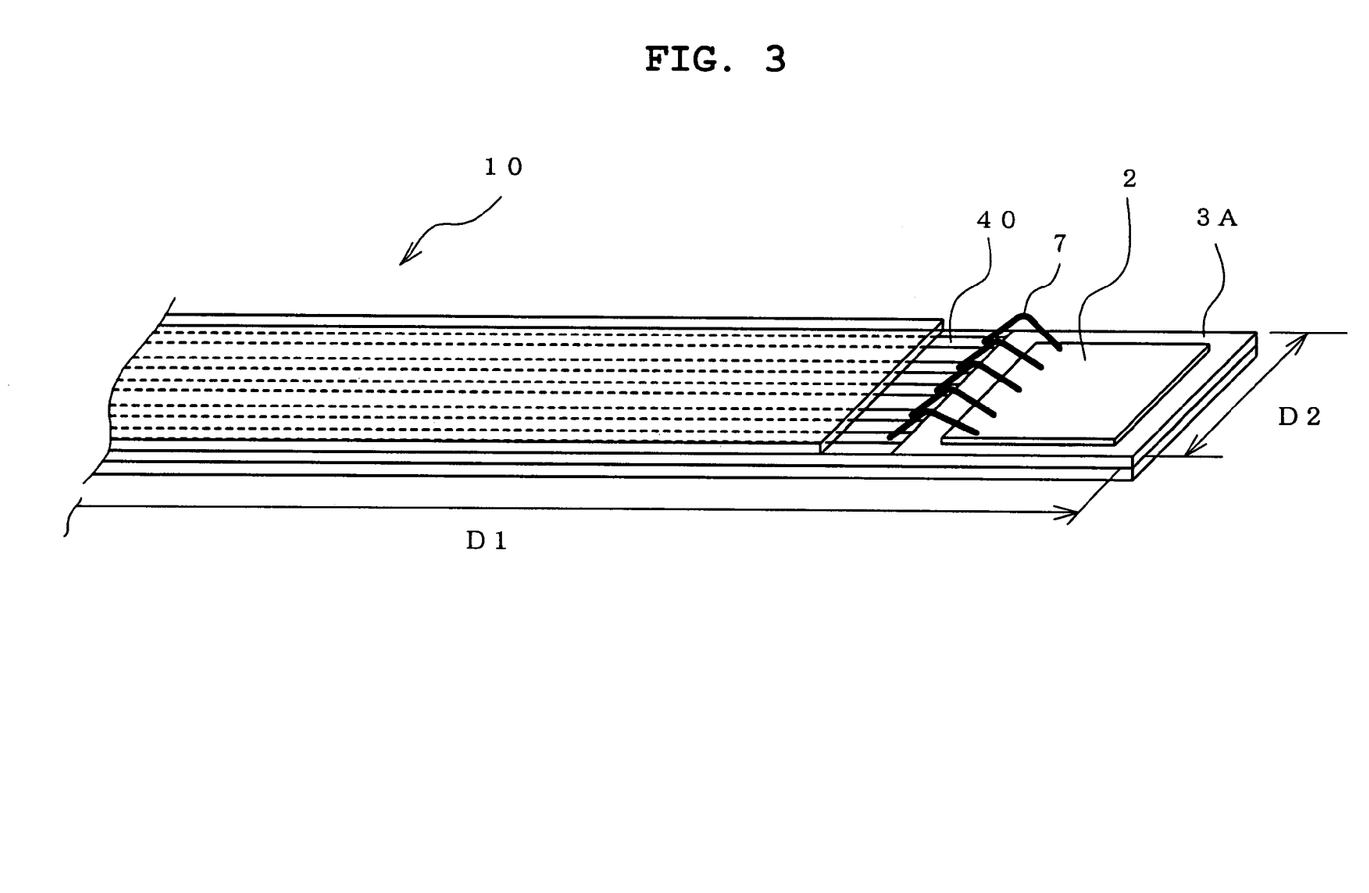
FIG. 3 is a perspective view of the flexible printed circuit board shown in FIG. 1 and FIG. 2 (one embodiment of the flexible printed circuit board to be used in the present invention).

FIGS. 1-3 show one embodiment of a catheter of the present invention, wherein FIG. 1 is a cross-sectional view (longitudinal cross-sectional view) along a plane including the axis of the catheter, FIG. 2 is a cross-sectional view (transverse cross-sectional view) along a plane perpendicular to the axis of the catheter, and FIG. 3 is a perspective view of the flexible printed circuit board shown in FIGS. 1, 2. While FIG. 1 shows only the anterior end 1A of a tube 1 and a section extending therefrom for some length, a flexible printed circuit board 10 is a long product that extends to be connected to the posterior end (not shown) of tube 1.

As shown in said embodiment of catheter 100, the catheter of the present invention is mainly characterized in that the catheter has a tube 1, the tube 1 comprises an electronic component 2 therein, and a signal line electrically connected to the electronic component 2 mounted in the tube 1 is constituted by a wiring pattern 4 of a flexible printed circuit board 10 inserted in the tube 1.

As explained in the "BACKGROUND OF THE INVENTION", in a catheter comprising an electronic component in a tube, after insertion of the catheter in the body of patients, an electrical signal sent by an electronic component in the anterior end or an intermediate part of the tube is processed by a measuring apparatus etc. connected to the posterior end of the tube outside the body of patients. When the operation of the electronic component is to be controlled, it is remotely controlled by a control device connected to the posterior end of a tube outside the body of patients.

Therefore, in said embodiment of catheter 100, too, flexible printed circuit board 10 inserted in the tube 1 extends from the vicinity of the position of the electronic component 2 in the tube 1 to the posterior end (not shown) of the tube 1, and an end of a wiring pattern 4, which is a signal line, is electrically connected to a measuring apparatus, a control device etc. (not shown) at the posterior end of the tube 1.

In other words, as shown in said embodiment of catheter 100, in the catheter of the present invention, a signal line that extends from the anterior end of the tube 1 to be the body of the catheter or the vicinity of the mounted electronic component 2 (installed part) in an intermediate part to the posterior end of the tube 1 is constituted by a wiring pattern 4 of the flexible printed circuit board 10. By this constitution, multiple signal lines can be used without greatly increasing the size of the tube 1.

In the case of conventional catheters using a signal cable as a signal line to be connected to an electronic component, when the number of signal cables is increased to contain multiple signal lines, a bundle of signal cables occupies a large volume, and the presence of multiple signal cables requires a considerable increase in the size of a tube. In contrast, the catheter of the present invention does not require a considerable increase in the size of a tube to increase the number of signal lines. This is because the signal line to be electrically connected to an electronic component is a wiring pattern of the flexible printed circuit board inserted in a tube, and the flexible printed circuit board permits increase in the number of wiring patterns without extremely enlarging its size.

The flexible printed circuit board (FPC) to be used for the catheter of the present invention has a basic constitution of a lamination structure wherein, as the flexible printed circuit board 10 used for the aforementioned one embodiment of catheter 100 (FIG. 1-FIG. 3), a base insulating layer 3, a wiring pattern 4 and a cover insulating layer 5 are laminated in this order.

The materials of the base insulating layer 3, wiring pattern 4 and cover insulating layer 5 can be known materials used for conventional flexible printed circuit boards.

As the material of the base insulating layer 3, for example, polyimide resin, polyester resin, epoxy resin, urethane resin, polystyrene resin, polyethylene resin, polyamide resin, acrylonitrile-butadiene-styrene (ABS) copolymer resin, polycarbonate resin, silicone resin, fluorine resin and the like can be mentioned. Of these, polyimide resin is preferable from the aspects of heat resistance, size stability, chemical resistance and the like. The thickness of the base insulating layer 3 is preferably about 5-100 µm, more preferably about 8-30 µm, from the aspects of flexibility and electrical insulation.

As the material of the wiring pattern 4, for example, stainless steel, copper, copper alloy, aluminum, copper-beryllium, phosphor bronze, 42 alloy and the like can be mentioned, with preference given to copper and copper alloy, from the aspects of conductivity and rigidity.

The thickness of the wiring pattern 4 is preferably 3-50 µm, more preferably 5-20 µm. When the thickness of the wiring pattern 4 is less than 3 µm, it is unpreferably susceptible to damage due to mechanical stress such as bending and the like, local pressure, wear and the like, and when it is greater than 50 µm, wiring at a fine pitch is difficult to achieve, and deformation does not occur easily.

The width of the wiring pattern 4 is preferably 5-100 µm, and the space between the adjacent wirings in multiple wiring patterns 4 is preferably as narrow as possible within the range free of inconveniences such as occurrence of unnecessary noise to electrical signals, short circuit due to metal ion migration and the like, and it is generally selected from the range of 5-100 µm.

A part (normally end 4A) of the wiring pattern 4 is not covered with a cover insulating layer 5, and used as a terminal part 40 for an electric connection with other conductor members such as metal wire and the like. Where necessary, the terminal part 40 may be coated with a highly conductive metal such as nickel, gold, solder, tin and the like.

Figure 8:
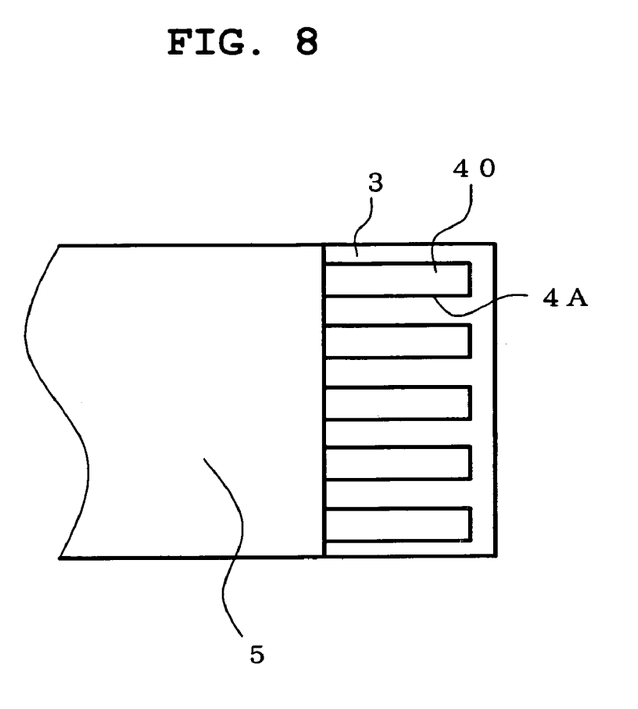
FIG. 8 is a plan view (seen from above) of the terminal part of the flexible printed circuit board shown in FIG. 3.
Figure 9:
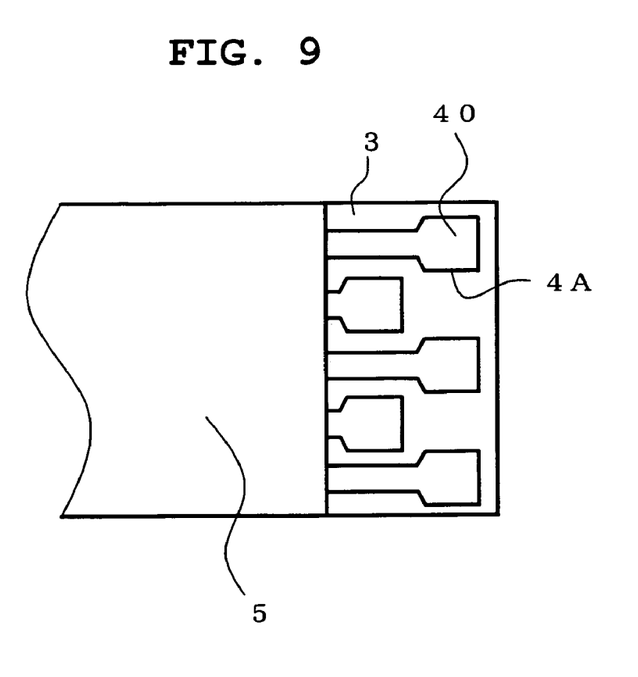
FIG. 9 is a plan view of another embodiment of arrangement of the terminal parts of the flexible printed circuit board to be used in the present invention.
Figure 10:
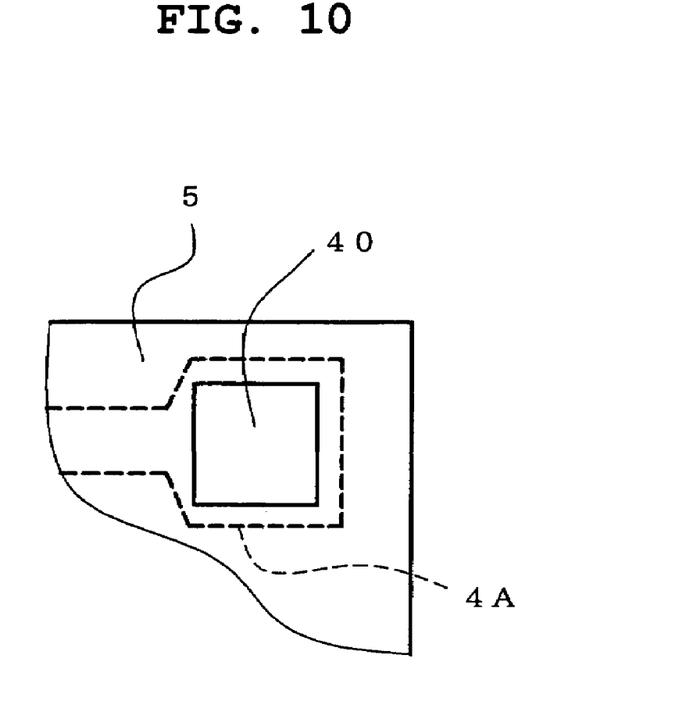
FIG. 10 is a plan view of another embodiment of exposure of terminal part of the flexible printed circuit board to be used in the present invention.

FIG. 8 is a plan view showing the vicinity of the end part 4A of multiple wiring patterns 4 in a flexible printed circuit board 10 of a catheter 100 of the aforementioned one embodiment. In the embodiment of FIG. 8, end parts 4A of the multiple wiring patterns 4 are aligned, and the terminal parts 40 of the respective wiring patterns are aligned in a single straight line. On the other hand, as in the embodiment of FIG. 9, the terminal part on the tip side and the terminal part on the posterior end side may be alternately arranged to form a pattern. The terminal parts 40 to be formed on the multiple wiring patterns 4 may be made to have a pattern formed by terminal parts having different positions alternately arranged as mentioned above, whereby, as shown in FIG. 9, the area of the terminal part 40 of each wiring pattern can be preferably enlarged and the connection with the below-mentioned metal wire and the like can be preferably facilitated. In the flexible printed circuit board 10 of the aforementioned one embodiment of catheter 100, the terminal part 40 is entirely exposed. As shown in FIG. 10, a part of the terminal part 40 may be exposed from an opening of a cover insulating layer 5.

The thickness of the cover insulating layer 5 is preferably 2-50 µm. When it is less than 2 µm, dispersion in the thickness and partial insulation failure tend to occur due to bending and wear, and when it exceeds 50 µm, flexibility tends to be degraded.

As the flexible printed circuit board (FPC) to be used in the present invention, one having a metal support plate 6 laminated on a plane opposite from the wiring pattern of the base insulating layer 3, like the flexible printed circuit board 10 used in the catheter of the aforementioned embodiment (FIGS. 1-3), is preferable. In the case of a flexible printed circuit board having such a metal support plate 6, insertion of a flexible printed circuit board into a tube is facilitated, since the metal support plate 6 increases the rigidity of the flexible printed circuit board as a whole. Moreover, unnecessary bending of the catheter and the like do not occur easily, and the catheter can be easily advanced in a desired direction in the body. As a result, the operability of insertion of the catheter into the body is improved.

As a material of the metal support plate 6, a single metal element such as stainless, steel, nickel, chrome, iron, tin, lead, aluminum and the like and an alloy of two or more from these metals and the like can be mentioned. Of these, stainless steel is preferable in view of its high elastic modulus.

The elastic modulus of the metal support plate 6 is preferably not less than 50 GPa, more preferably not less than 100 GPa, in consideration of insertability of a flexible printed circuit board into a tube and operability of catheter. However, when the elastic modulus is too high, the metal support plate is difficult to bend after insertion into a tube or lacks flexibility. Thus, the elastic modulus is preferably not more than 400 GPa, more preferably not more than 300 GPa. As used herein, the "elastic modulus" means tensile elasticity as measured under the test conditions of test piece width 20 mm, distance between chucks 100 mm, tension rate 50 mm/min.

The thickness of the metal support plate 6 is generally preferably about 10-200 μm (more preferably 20-50 μm). When the thickness of the metal support plate is less than 10 μm, a flexible printed circuit board easily develops curls and swelling, which in turn may render insertion of the flexible printed circuit board into a tube difficult. On the other hand, when it is thicker than 200 μm, flexibility of a flexible printed circuit board is degraded, which in turn may render insertion of the flexible printed circuit board into a tube difficult, and production by a roll to roll method (wherein a film (sheet) unwound from a roll is wound around a reeling roll, during which the film (sheet) is processed) becomes difficult to achieve.

In an Embodiment using the above-mentioned metal support plate 6, the metal support plate 6 can also be processed into a given pattern as necessary and utilized as a wiring pattern. In this case, the flexible printed circuit board becomes a double-sided printed (circuit) board, and wiring patterns formed on both sides of the base insulating layer can be utilized as signal lines. By the use of such a flexible printed circuit board having a double-sided printed structure, a catheter having electronic components on both sides of a flexible printed circuit board can be manufactured. When such metal support plate is used as a wiring pattern, the width of one wiring pattern is preferably about 10-500 μm, and the space between the adjacent wiring patterns is preferably about 10-300 μm.

In the present invention, the total thickness of the flexible printed circuit board (for both the presence of a metal support plate and absence thereof) is preferably 20-300 μm, more preferably 30-100 μm. When the total thickness is smaller than 20 μm, insertion into a tube becomes difficult due to degraded handling property. When the total thickness is greater than 300 μm, the flexibility of catheter is degraded, and operability during insertion of the catheter into the body is degraded.

The size (D1 in FIG. 3) of a flexible printed circuit board in the longitudinal direction (axis direction) is determined according to the length of the tube 1 from the electronic component mounting (installing) position to the posterior end of the tube 1 in the axis direction. In the following, the size of each part in the longitudinal direction is referred to as a "length". The length of the flexible printed circuit board needs to be the same as or not less than the length of from the electronic component mounting (installing) position to the posterior end of the tube 1 along the axis direction of the tube 1, which is generally within the range of 50-1000 mm.

In addition, the size of the flexible printed circuit board in the shorter side direction (D2 in FIG. 3) is preferably 100-3000 μm, more preferably 200-1500 μm. In the following, the size of each part in the short side direction is referred to as a "width". When the width of the flexible printed circuit board is smaller than 100 μm, the self supportability of the flexible printed circuit board is degraded and insertion into a tube becomes difficult. When it is greater than 3000 μm, the inner diameter and the outer diameter of the tube, in which to insert a flexible printed circuit board, becomes unpreferably large. The width is preferably smaller by about 50-100 μm than the inner diameter of a tube so as to facilitate insertion into the tube.

When a flexible printed circuit board has a metal support plate 6, the width of the metal support plate 6 is preferably 50-2950 μm.

Figure 4:
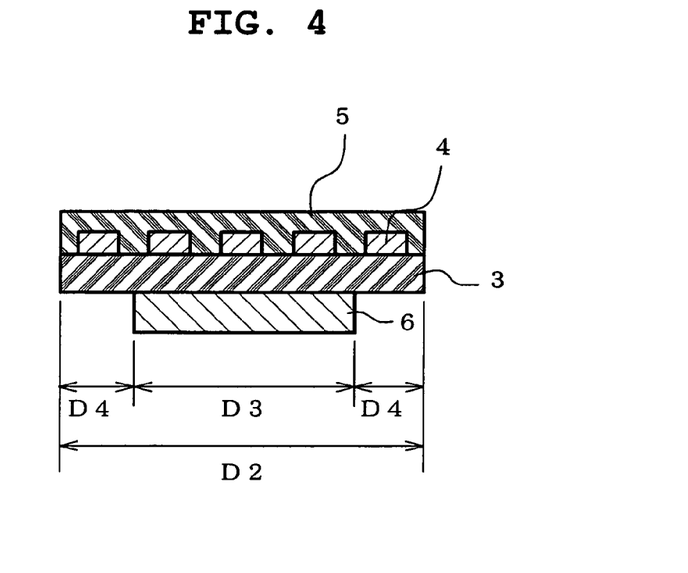
FIG. 4 is a cross-sectional view of another embodiment of the flexible printed circuit board to be used in the present invention.
Figure 5:
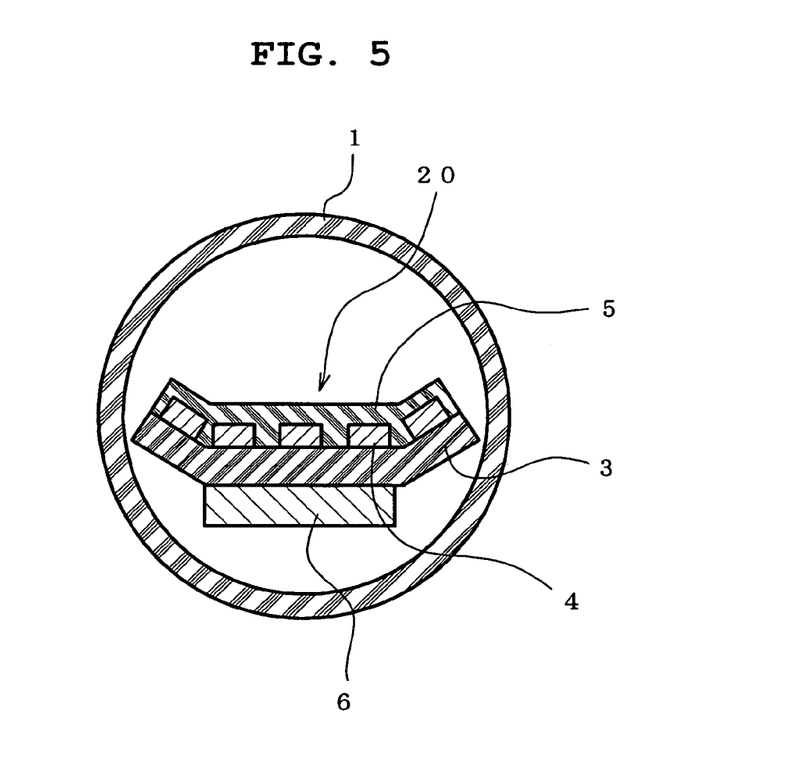
FIG. 5 is a cross-sectional view (transverse cross-sectional view), along the plane perpendicular to the axis of the catheter, of the catheter containing the flexible printed circuit board shown in FIG. 4 inserted in a tube.

In the flexible printed circuit board 10 used in the catheter 100 (FIG. 1-FIG. 3) of the aforementioned embodiment, the width of a metal support plate 6 (D3 in FIG. 2) is the same as the width (D2) of the flexible printed circuit board 10 (base insulating layer 3). In contrast, in a flexible printed circuit board 20 in the embodiment of FIG. 4, the width (D3) of the metal support plate 6 is smaller than the width (D2) of the base insulating layer 3, and therefore, both ends (edges on both sides) of the flexible printed circuit board in the short side direction do not have a metal support plate 6. By the use of a flexible printed circuit board having such structure, as shown in FIG. 5, edges on both sides of a base insulating layer 3 of a flexible printed circuit board 20 can be folded inside and the board having a reduced width can be inserted into the tube 1, thus further reducing the size of tube 1. In addition, damage on the inner wall of the tube during insertion of a flexible printed circuit board into the tube 1 can be prevented.

As mentioned above, in an embodiment free of a metal support plate 6 on the edge parts on both sides, the width (D4 in FIG. 4) of the part free of a metal support plate 6 is preferably 20-1000 μm. When the width is less than 20 μm, even a slight decrease in the processing precision results in partial exposure of both ends of a metal support plate to sometimes damage the inner wall of a tube, and when the width exceeds 1000 μm, the metal support plate may not be able to support the flexible printed circuit board sufficiently.

As the material of the tube 1 to be the main body of the catheter of the present invention, insulating resin materials such as fluororesins (e.g., polytetrafluoroethylene etc.), silicone resin, high density polyethylene resin, polyurethane resin, polyester resin, polyvinyl chloride and the like are used. In consideration of the flexibility, heat resistance, chemical resistance, biocompatibility, processability into tube and the like, fluororesin is preferable.

While the shape of the section (transverse section) perpendicular to the axis of the tube 1 is not particularly limited, a shape free of corners such as circle, ellipse and the like are preferable (generally circle). Taking a circle as an example, the inner diameter thereof is preferably about 0.2-3.5 mm, and the outer diameter thereof is preferably about 0.3-4 mm. When the inner diameter and the outer diameter of a tube are within the preferable ranges, a catheter superior in insertability of a flexible printed circuit board and operability of the catheter in the body of patients, which does not easily cause pain during operation of the catheter in the body of patients, can be realized. The inner diameter and the outer diameter are preferably determined to make the thickness of the tube 0.05-1.0 mm.

When a tube having a sectional shape other than a circle is used, it is preferable that the tube have a section whose maximum diameter of the inner circumference and maximum diameter of the outer circumference are within the preferable numerical ranges of the inner diameter and outer diameter of the above-mentioned circular section.

In the catheter of the present invention, the length (length in the axis direction) of the tube is generally not less than 30 mm, and further, not less than 100 mm, and the upper limit is generally not more than 1000 mm.

In the catheter of the present invention, as an electronic component 2 to be mounted in the tube 1, electronic components conventionally used for electronic component-loaded catheters can be used. Specifically, heat element, pressure sensor, thermistor for temperature measurement, ultrasonic oscillator, piezoelectric element and the like can be mentioned. The catheter 100 of the embodiment shown in FIG. 1-FIG. 3 comprises a pressure sensor as an electronic component 2. When a catheter mounting a pressure sensor is produced, as shown in FIG. 1, the pressure sensor (electronic component 2) is disposed such that sensitive surface 2A is exposed from a through hole H formed on a side wall of a tube.

In the catheter of the present invention, the connection (electric connection) between the electronic component and the flexible printed circuit board (wiring pattern) is formed, for example, by a method comprising, as shown in FIG. 1, metal welding of a terminal part 40 of a wiring pattern 4 of a flexible printed circuit board and a terminal (not shown) of an electronic component 2, as in respective bonding of one end and the other end of a metal wire 7, a method comprising covering both a terminal part 40 formed in a wiring pattern and a terminal of the electronic component with a conductive adhesive layer and the like. As shown in FIG. 1, the connection between the terminal part 40 of a wiring pattern 4 and a terminal of the electronic component 2 is preferably protected by sealing with a resin 8. As the resin 8 for sealing, for example, epoxy resin, fluorine resin, silicone resin and the like can be mentioned.

For fixing an electronic component 2 in a tube 1, as in the catheter 100 in one embodiment shown in FIG. 1-FIG. 3, the electronic component 2 is preferably mounted (fixed) on a terminal part 40 formed in a wiring pattern 4 on a base insulating layer 3 of a flexible printed circuit board 10, and a nearby area 3A free of wiring patterns. In this way, the wiring pattern 4 and the electronic component 2 both follow movements of a flexible printed circuit board 10, thereby minimizing the load on the connection part between them, and the connection reliability between the terminal of electronic component 2 and terminal part 40 of a wiring pattern 4 is improved.

For mounting (fixing) an electronic component 2 on a base insulating layer 3, for example, as shown in FIG. 1, a resin 8 is used for sealing the connection between a terminal part 40 formed on a wiring pattern 4 and the terminal of the electronic component 2, wherein the resin 8 is applied to an about entire side surface of the electronic component 2, bridging the surface of the base insulating layer 3 and the periphery of the electronic component 2. By this constitution, mounting (fixing) of an Electronic component 2 and connection of a terminal of the electronic component to a wiring pattern can be simultaneously performed efficiently. The electronic component 2 may be fixed with an adhesive in an area 3A near the terminal part 40 formed in the wiring pattern 4 on a base insulating layer.

As in the catheter 100 of one embodiment shown in FIG. 1-FIG. 3, when a catheter having a part of an electronic component 2 exposed from a through hole H formed on the side wall of a tube 1 is produced, it is preferable to apply a sealing resin 9 to cover the periphery of tube walls around the through hole H and an upper surface of the electronic component 2, so as to certainly block the inside of the tube from the outside thereof.

Figure 11:
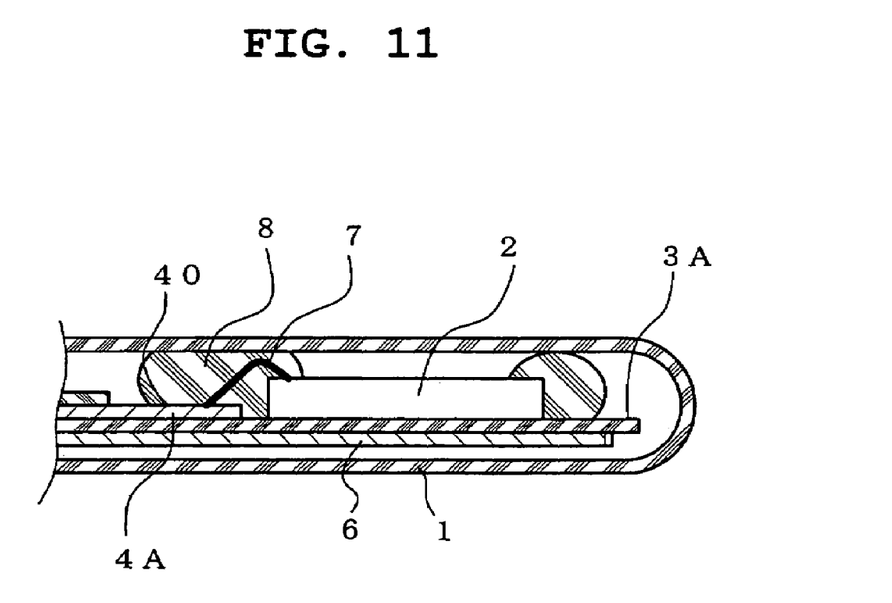
FIG. 11 is a cross-sectional view of the main parts enclosing an electronic component in a tube of the catheter of the present invention.

As the resin 9 for sealing, for example, epoxy resin, fluororesin, silicone resin and the like are used. When the sensitive surface of the electronic component 2 does not need to be exposed to the outside a tube, as in a temperature sensor, as shown in FIG. 11, tube walls may not have a through hole and the electronic component 2 may be enclosed in the tube 1. In this case, a resin for sealing is not necessary.

In the catheter 100 of one embodiment shown in FIG. 1-FIG. 3, a flexible printed circuit board 10 has a single layer of a conductor layer (wiring pattern 4). As a flexible printed circuit board, a multi-layer flexible printed circuit board wherein multiple conductor layers are connected via hole may be used. In the case of a multi-layer flexible printed circuit board, a greater number of wirings and terminals can be installed, and therefore, a greater number of electronic components can be mounted, which in turn enables functional improvement of catheter.

The production method of the flexible printed circuit board to be used in the present invention is not particularly limited, and the board can be produced by an appropriate combination of known membrane (layer) forming techniques, membrane (layer) patterning techniques, wiring formation techniques and photolithography techniques for printing etc. and the like, conventionally employed for the manufacture of flexible printed circuit boards. For example, subtractive method, semi-additive method and the like can be employed for the production.

When a base insulating layer 3 and a cover insulating layer 5 are formed in a given pattern, for example, a method using a photosensitive resin (e.g., photosensitive polyimide etc.) (namely, a photosensitive resin (precursor) layer is subjected to exposure, development, heat curing treatment and the like to form an insulating resin layer in a given pattern), a method comprising subjecting an insulating resin layer to etching by laser or with plasma to form a given pattern and the like can be mentioned. In view of workability, positioning accuracy and the like, a method using a photosensitive resin is preferable.

For production of a flexible printed circuit board having a metal support plate 6, a flexible printed circuit board having a base insulating layer 3, a wiring pattern 4 and a cover insulating layer 5 laminated in this order is produced, and the metal support plate 6 may be adhered to the base insulating layer 3 with an adhesive, or the base insulating layer 3, the wiring pattern 4 and the cover insulating layer 5 may be laminated in this order on the metal support plate 6.

When a flexible printed circuit board having a metal support plate 6 and free of a metal support plate on both ends of a substrate in the short side direction, or a flexible printed circuit board comprising a metal support plate as a wiring pattern is to be produced, a laminate structure comprising a metal support plate 6 is produced and then the metal support plate 6 is partly etched.

While the production method of the catheter of the present invention is not particularly limited, it is preferably produced by the following method.

For example, a catheter 100 of the embodiment shown in FIG. 1-FIG. 3 can be produced by a method comprising the following steps 1-3.

(step 1) a step of preparing a tube 1 having a through hole H formed on a side wall at a position corresponding to the position where an electronic component is mounted (the anterior end of a tube or an intermediate part thereof) and a flexible printed circuit board 10 whose size in the longitudinal direction is equivalent to or not less than the length from the through hole H to the posterior end of the tube 1, and inserting, in the tube, the flexible printed circuit board 10, (step 2) a step of mounting, through the hole H formed on a side wall of the tube 1, an electronic component 2 in an area 3A (area free of wiring pattern formation) near the terminal part 40 formed in a wiring pattern 4 on a base insulating layer 3 of the flexible printed circuit board 10, and (step 3) a step of connecting a terminal of the electronic component 2 and the terminal part 4A formed on the wiring pattern 4 by metal welding or with a conductive adhesive, and sealing the connection part with a resin.

It is also possible to mount an electronic component on a base insulating layer 3 of a flexible printed circuit board 10 and connect a terminal of the electronic component 2 and a terminal part 40 formed in a wiring pattern 4 by metal welding or with a conductive adhesive in advance, and then insert the flexible printed circuit board into a tube 1 and seal, with a resin, a connection part between the terminal of the electronic component 2 and the terminal part 40 formed in the wiring pattern 4 through a through hole H formed on a side wall of the tube 1.

When a catheter of the type free of exposure of a part of an electronic component, from a side wall of the tube, is to be produced, an electronic component is mounted on a base insulating layer of a flexible printed circuit board, a terminal of the electronic component and a terminal part formed in a wiring pattern are connected, the connection part is sealed with a resin and then the flexible printed circuit board is inserted in a tube.

EXAMPLES

The present invention is explained in more detail in the following by referring to Examples, which are not to be construed as limitative.

Example 1

In this Example, a flexible printed circuit board comprising five wiring patterns formed on a stainless steel substrate by a semi-additive method is manufactured, and the flexible printed circuit board is inserted in a tube to assemble a catheter. The flexible printed circuit board has the same structure as the flexible printed circuit board 10 shown in FIG. 3.

(Manufacture of Flexible Printed Circuit Board)

First, a photosensitive polyimide precursor 3' was applied onto a stainless steel substrate (SUS304) (length: 300 mm, width: 300 mm, thickness: 200 μm, elastic modulus: 205 GPa) as a metal support plate 6 (FIG. 6(a)), exposed, developed and heated to form multiple base insulating layers 3 comprising polyimide band having width of 500 μm, length of 200 mm and thickness of 10 μm in parallel (FIG. 6(b)).

Figure 6:
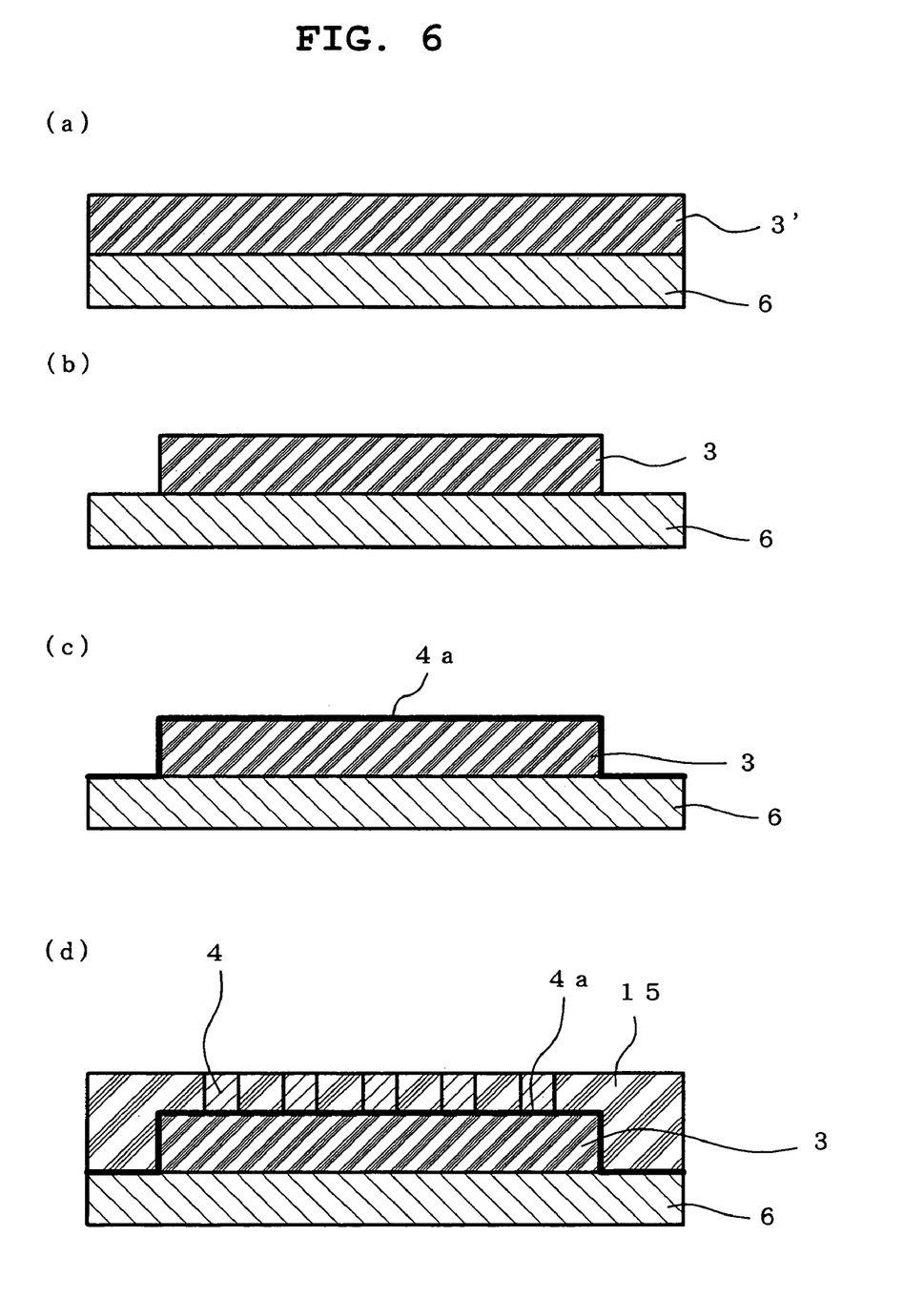

FIG. 6 shows only one base insulating layer 3 and the surrounding part thereof.

Secondly, a metal thin film (chrome thin film (thickness: 100 nm)/copper thin film (thickness: 100 nm)) 4a was formed (FIG. 6(c)) by continuous sputtering, and a mask for plating having a pattern reverse to the wiring pattern to be formed (namely, a pattern having an opening which is of the same pattern as the wiring pattern to be formed) 15 was formed by photoresist.

Figure 7:
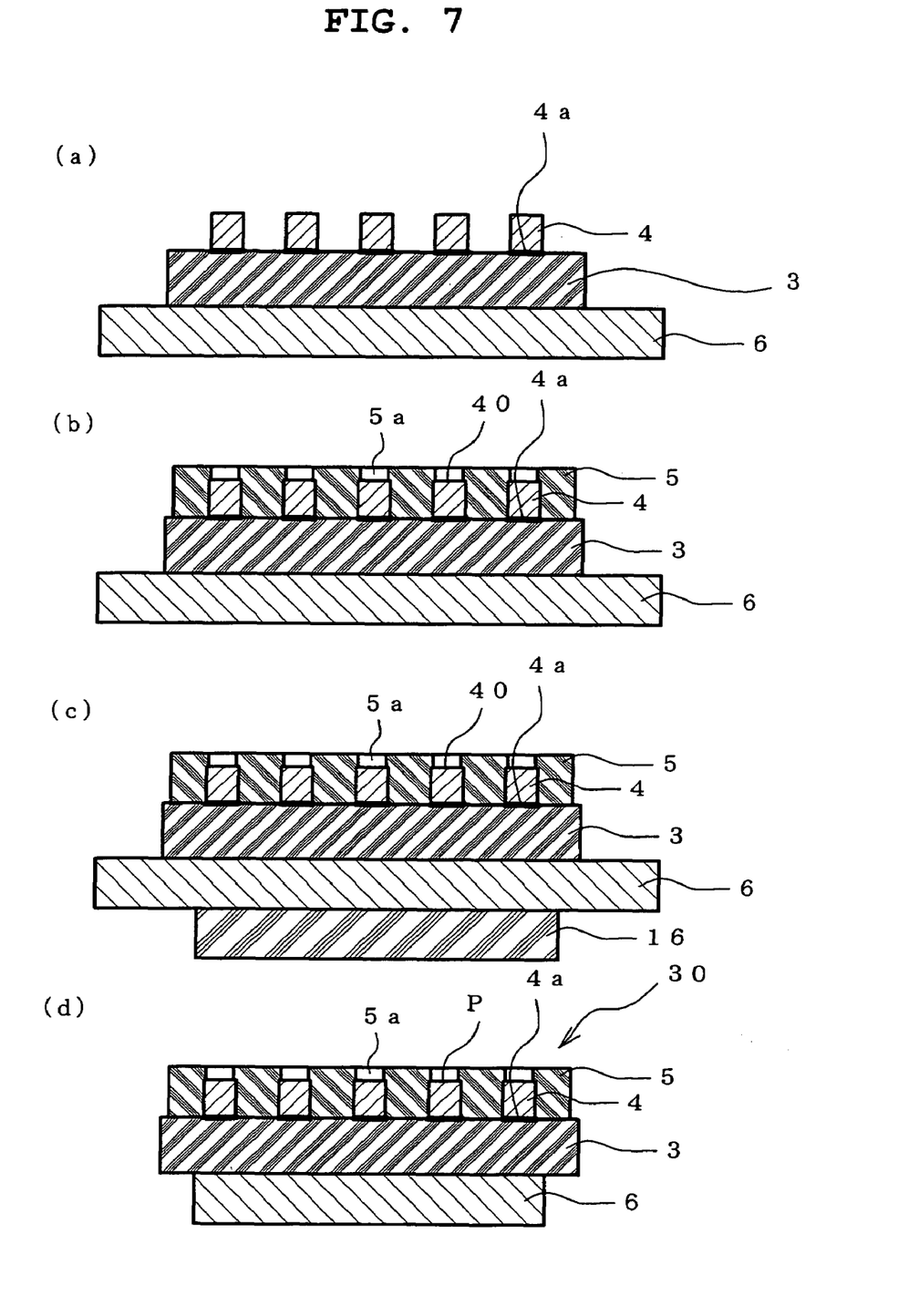

Then, a copper layer (thickness: 10 μm) was grown on a part free of a resist (opening of a mask for plating 15) by electrolytic copper plating, and five wiring patterns 4 running parallel to each other along the longitudinal direction of the base insulating layer 3 were formed (FIG. 6(d)), after which the mask for plating (resist) was peeled off and the exposed metal thin film 4a was removed by etching (FIG. 7(a)). The width of the copper wiring pattern 4 was 20 μm, the length (length in the axis direction) was 200 mm and a space between the adjacent patterns was 20 μm.

In the same manner as in the base insulating layer 3, coating with a photosensitive polyimide precursor, exposure, development and heating were successively performed, a cover insulating layer (thickness: 5 μm) 5 made from polyimide, which had a given pattern including an opening (part free of polyimide layer formation) 5a on a end part that became a terminal part of the copper wiring pattern 4 was formed, and a nickel (thickness: 5 μm)/gold (thickness: 0.2 μm) plating was applied to end part of the copper wiring pattern 4, which was exposed from the opening 5a of the cover insulating layer 5, to form a terminal part 40 (FIG. 7(b)).

Then, a photoresist pattern 16 was formed on a surface opposite from the surface where the base insulating layer 3 of the stainless substrate 6 was formed (FIG. 7(c)), and, using the photoresist pattern 16 as a mask, both ends of the stainless substrate 6 in the width direction were removed by etching. By removing the photoresist pattern 16, the both ends of the base insulating layer 3 in the width direction were protruded by 50 μm from the both ends (end part) of the stainless substrate 6 in the width direction. In this manner, a flexible printed circuit board 30 (width of base insulating layer 3: 500 μm, length of base insulating layer 3: 200 mm) having a metal support plate but free of metal support plate on both ends of the short side direction was completed (FIG. 7(d)).

Like the flexible printed circuit board 10 of one embodiment shown in FIG. 3, in the flexible printed circuit board 30, its end part on one side in the longitudinal direction (axis direction) was not covered with an insulating layer 5, and the terminal part 4, which was formed in the wiring pattern 3 on the exposed base insulating layer 3, and the vicinity thereof were the area for mounting (area for disposing) an electronic component.

(Assembly of Catheter)

A fluororesin tube (inner diameter 0.6 mm, outer diameter 0.8 mm, length (length in the axis direction) 200 mm) having one closed end and the other open end in the axis direction was prepared, and a through hole (a size of hole: 2 mm×0.4 mm (tetragonum)) was formed on a side wall of the tube at 5 mm from the aforementioned one end in the axis direction of the tube.

Then, a pressure sensor (size of the sensor: length 3 mm, width 0.5 mm, thickness: 250 μm, terminal size: tetragonum of 80 μm×80 μm) was disposed in an area near a terminal part formed in a wiring pattern on a base insulating layer of the flexible printed circuit board, a terminal (electrode) of the pressure sensor and the terminal formed in the wiring pattern were connected by wire bonding using a gold wire, a flexible printed circuit board was inserted from the other end in the axis direction of the above-mentioned tube, the connection part with the gold wire between the pressure sensor on the flexible printed circuit board and the wiring pattern was sealed with an epoxy resin through a through hole formed on a side wall of the tube, and a silicone resin for sealing was further applied to the surrounding area of the through hole in the tube and the gap between electronic components, whereby a catheter with a pressure sensor was manufactured.

While the thus-obtained catheter with a pressure sensor have multiple (five) wiring patterns, it showed superior flexibility and could be inserted into the body of a test subject (monitor) with fine operability. The test subject did not complain pain during insertion of the catheter.

Example 2

In the same manner as in Example 1 except that the stainless substrate was entirely removed from the flexible printed circuit board, a catheter with a pressure sensor was manufactured.

While the catheter with a pressure sensor showed lower workability as compared to the catheter with a pressure sensor of Example 1 during assembly thereof when the flexible printed circuit board was inserted in a tube, this catheter could be assembled without any problem. While the operability during insertion of the catheter into the body of a monitor was somewhat lower than the catheter with a pressure sensor of Example 1, the monitor did not complain pain during insertion of the catheter.

According to the present invention, increase in the size of a tube of an electronic component-loaded catheter can be reduced and the catheter can be produced highly efficiently.

The present invention is based on patent application No. 363322/2004 filed in Japan, the contents of which are hereby incorporated by reference.

What is claimed is:

1. A catheter comprising:

a tube;

an electronic component set in an anterior end or an intermediate part of the tube;

a flexible printed circuit board inserted in the tube, the flexible printed circuit board comprising a metal support plate, a base insulating layer, and a signal line electrically connected to the electronic component, the signal line extending through the tube, from a vicinity of the electronic component to a posterior end of the tube, wherein the signal line is formed as a wiring pattern of the flexible printed circuit board, wherein a size of the metal support plate in a width direction is smaller than a size of a base insulating layer in the width direction, and therefore, both edge parts of the flexible printed circuit board in the width direction are free of the metal support plate, wherein the flexible printed circuit board is disposed in the tube, with both edge parts, which are free of the metal support plate, folded inside, and wherein the width of each of the edge parts that are free of the metal support plate is 20-1000 μm.

2. A production method of a catheter according to claim 1, which method comprises a step of preparing the tube, wherein the tube has a through hole formed in a side wall at a position corresponding to the position where the electronic component is to be mounted, a step of preparing the flexible printed circuit board, wherein the size of the flexible printed circuit board in the longitudinal direction is equivalent to or not less than the length from the through hole to the posterior end of the tube, and the flexible printed circuit board has the metal support plate whose size in the width direction is smaller than that of the base insulating layer in the width direction, and therefore, both ends of the flexible printed circuit board in the width direction are free of the metal support plate, a step of inserting the flexible printed circuit board in the tube, such that the parts free of the metal support plate are folded inside, a step of mounting, through the through hole formed on the side wall of the tube, the electronic component in an area near the terminal part formed in the wiring pattern on the base insulating layer of the flexible printed circuit board, and a step of connecting a terminal of the electronic component and the terminal part formed on the wiring pattern by metal welding or with a conductive adhesive, and sealing the connection part with a resin, wherein the width of each of the edge parts that are free of the metal support plate is 20-1000 μm.

3. A production method of a catheter according to claim 1, which method comprises a step of preparing the tube, wherein the tube has a through hole formed in a side wall at a position corresponding to the position where the electronic component is to be mounted, a step of preparing the flexible printed circuit board, wherein the size of the flexible printed circuit board in the longitudinal direction is equivalent to or not less than the length from the through hole to the posterior end of the tube, and the flexible printed circuit board has the metal support plate whose size in the width direction is smaller than that of the base insulating layer in the width direction, and therefore, both ends of the flexible printed circuit board in the width direction are free of the metal support plate, a step of mounting the electronic component in an area near a terminal part formed on the wiring pattern on the base insulating layer of the flexible printed circuit board, then connecting a terminal of the electronic component and the terminal part formed in the wiring pattern by metal welding or with a conductive adhesive, a step of inserting the flexible printed circuit board with the electronic component mounted thereon in the tube, such that the parts free of the metal support plate are folded inside, and a step of sealing the connection part between the terminal of the electronic component and the terminal part formed on the wiring pattern with a resin through the through hole formed on the side wall of the tube, wherein the width of each of the edge parts that are free of the metal support plate is 20-1000 μm.

4. A catheter comprising:

a tube;

an electronic component set in an anterior end or an intermediate part of the tube;

a flexible printed circuit board inserted in the tube, the flexible printed circuit board comprising a metal support plate, a base insulating layer, and a signal line electrically connected to the electronic component, the signal line extending through the tube, from a vicinity of the electronic component to a posterior end of the tube, wherein the signal line is formed as a wiring pattern of the flexible printed circuit board, wherein a size of the metal support plate in a width direction is smaller than a size of a base insulating layer in the width direction, and therefore, both edge parts of the flexible printed circuit board in the width direction are free of the metal support plate, wherein the flexible printed circuit board is disposed in the tube, with both edge parts, which are free of the metal support plate, folded inside, and wherein the size of the metal support plate in the width direction is 50-2950 μm, and the size of the base insulating layer in the width direction is 100-3000 μm.

5. The catheter of claim 1 or 4, wherein the wiring pattern is provided on the base insulating layer of the flexible printed circuit board, and the wiring pattern has a terminal part, the electronic component is installed in an area near the terminal part, a terminal of the electronic component and the terminal part formed in the wiring pattern are connected by metal welding or with a conductive adhesive, and the connection part is sealed with a resin.

6. The catheter of claim 1 or 4, wherein the wiring pattern is provided on the base insulating layer of the flexible printed circuit board, and the wiring pattern has a terminal part, and the terminal part has a pattern formed by a first terminal part and a second terminal part, wherein the first terminal part is positioned nearer to the anterior end of the tube than the second terminal part.

7. The catheter of claim 1 or 4, wherein the wiring pattern on the base insulating layer of the flexible printed circuit board has a terminal part, the electronic component is mounted in an area near the terminal part, and a through hole is formed in a side wall of the tube at a position corresponding to the electronic component.

8. A production method of a catheter according to claim 4, which method comprises a step of preparing the tube, wherein the tube has a through hole formed in a side wall at a position corresponding to the position where the electronic component is to be mounted, a step of preparing the flexible printed circuit board, wherein the size of the flexible printed circuit board in the longitudinal direction is equivalent to or not less than the length from the through hole to the posterior end of the tube, and the flexible printed circuit board has the metal support plate whose size in the width direction is smaller than that of the base insulating layer in the width direction, and therefore, both ends of the flexible printed circuit board in the width direction are free of the metal support plate, a step of inserting the flexible printed circuit board in the tube, such that the parts free of the metal support plate are folded inside, a step of mounting, through the through hole formed on the side wall of the tube, the electronic component in an area near the terminal part formed in the wiring pattern on the base insulating layer of the flexible printed circuit board, and a step of connecting a terminal of the electronic component and the terminal part formed on the wiring pattern by metal welding or with a conductive adhesive, and sealing the connection part with a resin, wherein the size of the metal support plate in the width direction is 50-2950 μm, and the size of the base insulating layer in the width direction is 100-3000 μm.

9. A production method of a catheter according to claim 4, which method comprises a step of preparing the tube, wherein the tube has a through hole formed in a side wall at a position corresponding to the position where the electronic component is to be mounted, a step of preparing the flexible printed circuit board, wherein the size of the flexible printed circuit board in the longitudinal direction is equivalent to or not less than the length from the through hole to the posterior end of the tube, and the flexible printed circuit board has the metal support plate whose size in the width direction is smaller than that of the base insulating layer in the width direction, and therefore, both ends of the flexible printed circuit board in the width direction are free of the metal support plate, a step of mounting the electronic component in an area near a terminal part formed on the wiring pattern on the base insulating layer of the flexible printed circuit board, then connecting a terminal of the electronic component and the terminal part formed in the wiring pattern by metal welding or with a conductive adhesive, a step of inserting the flexible printed circuit board with the electronic component mounted thereon in the tube, such that the parts free of the metal support plate are folded inside, and a step of sealing the connection part between the terminal of the electronic component and the terminal part formed on the wiring pattern with a resin through the through hole formed on the side wall of the tube, wherein the size of the metal support plate in the width direction is 50-2950 μm, and the size of the base insulating layer in the width direction is 100-3000 μm.

* * * * *